US011467117B2

(12) United States Patent
Ashida

(10) Patent No.: US 11,467,117 B2
(45) Date of Patent: Oct. 11, 2022

(54) SENSOR ARRAY

(71) Applicant: SHARP KABUSHIKI KAISHA, Sakai (JP)

(72) Inventor: Nobuyuki Ashida, Sakai (JP)

(73) Assignee: SHARP KABUSHIKI KAISHA, Sakai (JP)

( * ) Notice: Subject to any disclaimer, the term of this patent is extended or adjusted under 35 U.S.C. 154(b) by 325 days.

(21) Appl. No.: 16/631,817

(22) PCT Filed: Jun. 4, 2018

(86) PCT No.: PCT/JP2018/021396
§ 371 (c)(1),
(2) Date: Jan. 16, 2020

(87) PCT Pub. No.: WO2019/017094
PCT Pub. Date: Jan. 24, 2019

(65) Prior Publication Data
US 2020/0166472 A1 May 28, 2020

(30) Foreign Application Priority Data
Jul. 19, 2017 (JP) .............................. JP2017-140137

(51) Int. Cl.
*G01N 27/22* (2006.01)
*G01N 27/447* (2006.01)
*B03C 5/00* (2006.01)

(52) U.S. Cl.
CPC ......... *G01N 27/228* (2013.01); *G01N 27/221* (2013.01); *G01N 27/447* (2013.01); *B03C 5/005* (2013.01)

(58) Field of Classification Search
CPC .. G01N 27/228; G01N 27/221; G01N 27/447; G01N 27/02; G01N 27/227; G01N 27/416; G01N 27/26; B03C 5/005; B03C 5/02; B03C 2201/26; C12M 1/34
See application file for complete search history.

(56) References Cited

U.S. PATENT DOCUMENTS

| 2011/0091864 A1* | 4/2011 | Karlsson .......... G01N 27/44747 435/4 |
| 2011/0108422 A1 | 5/2011 | Heller et al. |
| 2015/0083613 A1* | 3/2015 | Lee ..................... G01N 27/3272 204/403.01 |
| 2015/0276649 A1* | 10/2015 | Farrow ................ G01N 33/483 205/792 |

(Continued)

FOREIGN PATENT DOCUMENTS

| JP | 2004135512 A * | 5/2004 | .......... B01J 19/0046 |
| JP | 3669182 B2 | 7/2005 | |
| JP | 2008-525797 A | 7/2008 | |

(Continued)

*Primary Examiner* — Feba Pothen
(74) *Attorney, Agent, or Firm* — ScienBiziP, P.C.

(57) ABSTRACT

There is provided an impedance sensor capable of counting the number of microscopic biological materials and specifying their properties stably with high sensitivity. An impedance sensor includes a measuring electrode pair formed at a wiring layer in a multilayer-wiring circuit board and one or more dielectrophoresis electrodes formed at another wiring layer lower than the wiring layer.

3 Claims, 10 Drawing Sheets

(56) References Cited

U.S. PATENT DOCUMENTS

2019/0025235 A1    1/2019   Mitsunaka et al.

FOREIGN PATENT DOCUMENTS

| JP | 2013-224947 A | 10/2013 | | |
|----|---------------|---------|----|----|
| JP | 2017-111044 A | 6/2017 | | |
| KR | 20150111246 A | * 10/2015 | ......... | G01N 33/5438 |
| WO | 2017/010182 A1 | 1/2017 | | |

* cited by examiner

1: IMPEDANCE SENSOR
10: SEMICONDUCTOR SUBSTRATE
11: INTERLAYER INSULATING FILM
12: SURFACE PROTECTION FILM
20: LC OSCILLATOR
30: MEASURING ELECTRODE PAIR
31: DIELECTROPHORESIS ELECTRODE PAIR
40: FREQUENCY DETECTOR
50: DIELECTROPHORESIS SIGNAL SOURCE

11: INTERLAYER INSULATING FILM
12: SURFACE PROTECTION FILM
70: BACTERIA (a)

(b)

1a: IMPEDANCE SENSOR
10: SEMICONDUCTOR SUBSTRATE
11: INTERLAYER INSULATING FILM
12: SURFACE PROTECTION FILM
20: LC OSCILLATOR
30: MEASURING ELECTRODE PAIR
31: DIELECTROPHORESIS ELECTRODE PAIR
40: FREQUENCY DETECTOR
50: DIELECTROPHORESIS SIGNAL SOURCE

SENSOR ARRAY

TECHNICAL FIELD

One aspect of the present invention relates to a sensor and a sensor array including a plurality of sensors.

BACKGROUND ART

Impedance sensors are used for specifying the number of microscopic biological materials such as microorganisms or cells and their properties. The meaning of impedance here covers not only the magnitude of complex impedance but also the case of targeting the capacitive property; in both cases, it is simply referred to as impedance. The size of a biological material as a test target is, for example, approximately 0.5 to 5 µm in the case of a bacterium and approximately 10 to 30 µm in the case of a cell. It is known that a frequency range of 30 to 200 GHz is preferable as the range used for measuring impedance. This is because the permittivity in the frequency range of 30 to 200 GHz greatly reflects the properties of a biological material (PTL 1).

PTL 1 discloses an impedance sensor using an oscillator formed at a semiconductor. The configuration of the impedance sensor described in PTL 1 is explained with reference to FIG. 9. An impedance sensor 100 includes an LC oscillator 200 involving a measuring electrode pair 300 formed at a semiconductor substrate 101 and a frequency detection circuit 400. When a test target is brought into contact with or proximity to the LC oscillator 200, in the impedance sensor placed in an atmosphere such as air or water, the parasitic capacitance of the measuring electrode pair 300 changes depending on the permittivity of the test target, and as a result, the oscillation frequency of the LC oscillator 200 changes. The frequency detection circuit 400 detects oscillation frequency. In accordance with the difference in oscillation frequency between the presence and absence of a particular test target, the permittivity of the particular test target is estimated. Since an LC oscillator formed at a semiconductor substrate is used, it is possible to detect impedance at high frequencies suitable for detecting biological materials.

Another technique for moving microscopic biological materials such as microorganisms and cells is dielectrophoresis. The dielectrophoresis is a phenomenon in which particles are polarized in a non-uniform alternating electric field due to the electric field and migrates in a stronger direction or a weaker direction with respect to the electric field intensity.

PTL 2 discloses a microorganism counter constituted by an impedance sensor using dielectrophoresis. The configuration of the impedance sensor used in PTL 2 is explained with reference to FIG. 10. As illustrated in FIG. 10, in the impedance sensor described in PTL 2, the electrodes of a measuring electrode pair 3000 are disposed on a glass substrate 1010 to nest inside one another. The measuring electrode pair 3000 is coupled to a dielectrophoresis signal source circuit 5000 in addition to a measuring unit 6000.

Next, the operation of the impedance sensor described in PTL 2 is explained. A sample liquid that contains microorganisms targeted for detection and with which the cell 7000 is filled flows onto the board on which the measuring electrode pair 3000 is placed. The measuring electrode pair 3000 is coupled to the dielectrophoresis signal source circuit 5000 and an alternating current signal (a dielectrophoresis signal) at a frequency and an amplitude that enable manipulation of microorganisms targeted for test is applied to the measuring electrode pair 3000, and as a result, the target microorganisms are collected between the measuring electrodes. The number of microorganisms accumulated between the measuring electrodes in a given time after the application of dielectrophoresis signal depends on the number of microorganisms that exist in the test sample liquid. In addition, an alternating current signal for measurement is applied to the measuring electrodes and the current value and the phase difference between voltage and current at the moment are measured, and accordingly, the impedance across the measuring electrodes is calculated. By comparing the calculated impedance with an impedance measurement result about a reference material containing a known number of microorganisms, the number of microorganisms contained in the test sample liquid are estimated. By employing dielectrophoresis, it is possible to collect more microorganisms between measuring electrodes in comparison to the case of not employing dielectrophoresis, and consequently, the number of microorganisms can be counted with a high sensitivity.

CITATION LIST

Patent Literature

PTL 1: International application publication pamphlet "International publication No. WO2017/010182 (published on Jan. 19, 2017)"

PTL 2: Japanese Patent "Japanese Patent No. 3669182 (published on May 9, 2000)"

SUMMARY OF INVENTION

Technical Problem

Concerning the known impedance sensor disclosed in PTL 1, in order to conform to design rules in a manufacturing factory and the demand for sensitive sensing, sensing can be performed in the range of approximately several to several tens µm close to the measuring electrode pair. Within the range, detection sensitivities (gains) are distributed depending on the position relative to the measuring electrode pair. As a result, when the impedance sensor of PTL 1 is used for detecting a biological material, such as a microorganism or a cell, with a size of 0.5 µm to 30 µm, in order to obtain a stable detection value with high sensitivity, it is necessary to securely fix the test target at an appropriate position with respect to the measuring electrode pair, but this is extremely difficult.

In the known impedance sensor used in the microorganism counting apparatus of PTL 2, the measuring electrode pair is utilized as a dielectrophoresis electrode pair, and as a result, microorganisms are collected in an area at which the electric field is strongest and non-uniform close to the dielectrophoresis electrode pair. However, since in the microorganism counting apparatus of PTL 2 the electrode for dielectrophoresis is identical to the electrode for measuring impedance, when impedance is measured while dielectrophoresis signal is applied, it is necessary to perform application and measurement at the same frequency and amplitude. When a signal at a frequency and an amplitude suitable for impedance measurement is used, dielectrophoresis cannot function during the measurement, and thus, the effect of collecting test targets is weakened.

As described above, concerning the related art, some points regarding sensitivity and stability in impedance measurement need to be improved.

One aspect of the present invention has been made in consideration of the problems described above, and an object thereof is to implement a sensor capable of measuring impedance of a target material stably with high sensitivity.

Solution to Problem

To address the problem described above, a sensor according to one aspect of the present invention includes a measuring electrode pair formed at a wiring layer in a multi-layer-wiring circuit board and one or more dielectrophoresis electrodes formed at another wiring layer lower than the wiring layer.

Advantageous Effects of Invention

A sensor according to one aspect of the present invention can measure impedance of a target material stably with high sensitivity.

DESCRIPTION OF EMBODIMENTS

Embodiment 1

Figure 1:
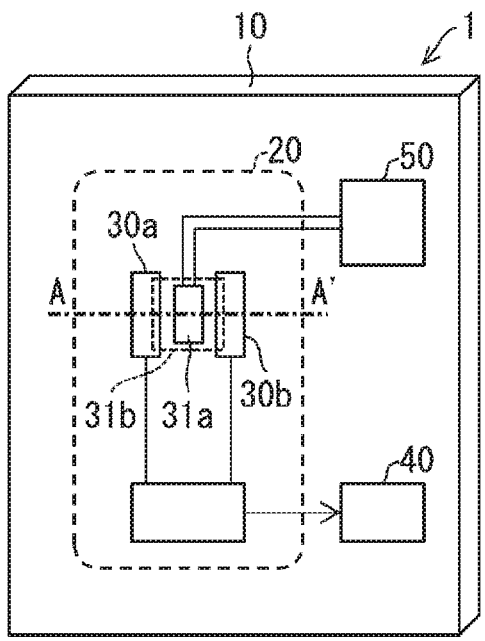
FIG. 1(a) is a block diagram illustrating a configuration of a sensor apparatus according to Embodiment 1 of the present invention and FIG. 1(b) is a sectional view taken along line A-A' in FIG. 1(a).
Figure 1:
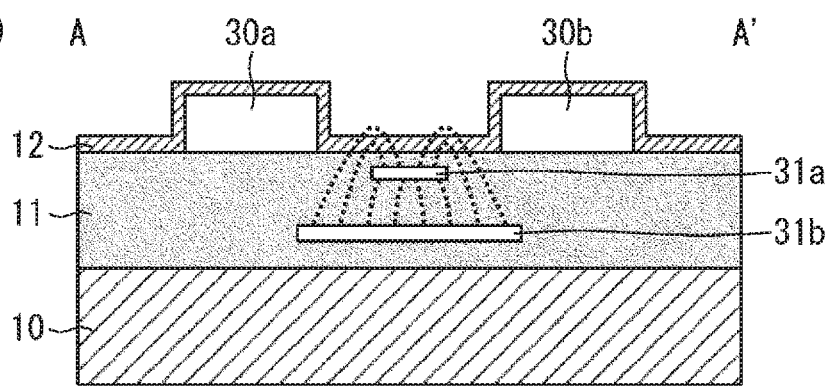

Embodiment 1 of the present invention is described with reference to FIG. 1. FIG. 1(a) is a block diagram illustrating a configuration of a sensor apparatus according to Embodiment 1 of the present invention.

An impedance sensor 1 includes an LC oscillator 20 involving a measuring electrode pair 30 (30a, 30b) constituted by plate electrodes facing a semiconductor substrate 10, a frequency detector 40, a dielectrophoresis electrode pair 31 (31a, 31b), and a dielectrophoresis signal source 50.

The LC oscillator 20 is constituted by an oscillator including a differential transistor pair, an inductor, and a capacitor that are positioned at the semiconductor substrate 10 and not illustrated in the drawing.

The measuring electrode pair 30 operates as part of the capacitor in the oscillator of the LC oscillator 20. In the semiconductor substrate 10, the circuit operation at high frequencies is achievable, and thus, the measuring electrode pair 30 can be suitably used for impedance measurement at high frequencies. The operation of the LC oscillator 20 has a general configuration and the description thereof is thus omitted. Another circuit configuration with the same function may be used as the LC oscillator 20.

The frequency detector 40 is constituted by a circuit for counting pulses that are inputted in a given period. The operation of the frequency detector 40 is a general configuration and the description thereof is thus omitted. Another circuit configuration with the same function may be used as the frequency detector 40.

The dielectrophoresis electrode pair 31 is coupled to the dielectrophoresis signal source 50.

While the frequency detector 40 and the dielectrophoresis signal source 50 are positioned at the semiconductor substrate 10, this configuration does not limit the present embodiment. The constituent elements of the frequency detector 40 and the dielectrophoresis signal source 50 may be partially or entirely positioned outside the semiconductor substrate.

Next, a positional relationship between the measuring electrode pair 30 and the dielectrophoresis electrode pair 31 and wiring layers that are used are described with reference to FIG. 1(b) that is a sectional view taken along line A-A' in FIG. 1(a).

As illustrated in FIG. 1(b), the measuring electrode pair 30 is formed at a wiring layer as a bonding pad that is the topmost wiring layer. Since fine formation is not necessary for the wiring layer as a bonding pad, the thickness can be greater than the thickness of wires in lower layers. The preferable thickness of the measuring electrode pair 30 is, for example, approximately 4 μm and preferably formed of a material such as aluminum.

Additionally, as illustrated in FIG. 1(b), the measuring electrode pair 30 is covered by a surface protection film 12. This can hinder the effect on impedance measurement due to electrolysis and corrosion or disconnection of the electrode when the conductivity of the solvent of the test material is relatively high.

The surface protection film 12 is formed of, for example, a silicon oxide film and a silicon nitride film and the total thickness is approximately 1 μm. Wiring layers under the wiring layer as a bonding pad are covered by an interlayer insulating film 11 and the interlayer insulating film 11 is flattened for each wiring layer not to have projections or depressions on the surface depending on the presence or absence of wire pattern of the wiring layer.

When the board is viewed from above, the dielectrophoresis electrode 31a, which is one electrode of the dielectrophoresis electrode pair 31, is formed between the electrodes (30a and 30b) of the measuring electrode pair 30 facing each other in a wiring layer (also referred to as a first wiring layer)

lower than a layer of the measuring electrode pair 30 (for example, one layer lower than a layer of the measuring electrode pair 30). The dielectrophoresis electrode 31b, which is the other electrode of the dielectrophoresis electrode pair 31, is positioned in another wiring layer (also referred to as a second wiring layer) lower than a layer of the first wiring layer and situated at a position at which the dielectrophoresis electrode 31b and the dielectrophoresis electrode 31a overlap when the board is viewed from above.

It should be noted that, when a low resistance substrate, such as silicon, is used as a multilayer-wiring board, the dielectrophoresis electrode 31b is not necessarily provided explicitly as will be described later as a modified example. In the case of such a configuration, it is preferable to use a silicon substrate coupled to a ground potential.

Dotted lines between the electrodes of the dielectrophoresis electrode pair in FIG. 1(b) represent lines of electric force in the case of applying a dielectrophoresis signal to the dielectrophoresis electrode pair 31.

Next, concerning an operation of the impedance sensor 1, an operation of impedance measurement is first described.

When the inductance of the resonance circuit of the LC oscillator 20 is L and the capacitance is C, an oscillation frequency f of the LC oscillator 20 is expressed as $f=2\pi/\sqrt{LC}$. In the impedance sensor 1 using the LC oscillator 20, when a test target is brought into contact with or proximity to the measuring electrode pair 30, the parasitic capacitance of the measuring electrode pair 30 changes depending on the permittivity of the test target. This change is detected by the frequency detector 40 as the change in oscillation frequency. A capacitance C between electrodes of an electrode pair with a dielectric of a permittivity E in between is expressed as $C=\varepsilon \times S/d$, where the area of the electrode is S and the distance is d. Thus, the detection sensitivity (gain) is relatively high in an area close to the electrodes between two measuring electrodes of the measuring electrode pair 30 facing each other (in other words, the detection sensitivity in the area is higher than the detection sensitivity in other areas). In the present embodiment, the measuring electrode pair 30 is thicker than the surface protection film 12. As a result, a space for positioning a test target is secured in an area with relatively high detection sensitivity (gain) between electrodes. It should be noted that, while in the above description, for ease of description, sensing operation has been described by focusing on capacitance, which is the real part of complex permittivity, another configuration may be used in which the change in the imaginary part of complex permittivity is detected in accordance with the change in oscillation frequency by designing the configuration of the measuring electrode pair and the surface protection film. The operation of impedance measurement is also the same in this case.

Next, a dielectrophoresis operation is described. As illustrated in FIG. 1(a), a signal at a suitable frequency and a suitable amplitude is applied by the dielectrophoresis signal source 50 to the dielectrophoresis electrode 31a so as to subject an object under examination to force that moves the object in a direction toward the stronger electric field. The frequency and amplitude can be set as appropriate depending on the test target that is desired to be manipulated. Usually, the frequency ranges from approximately several kHz to several MHz and the amplitude ranges from approximately 1 to 50 V. The electric field distribution illustrated in FIG. 1(b) appears by applying a dielectrophoresis signal, the test target is attracted close to an end portion of the dielectrophoresis electrode 31a at which the electric field is stronger and non-uniform.

A state of manipulation by the dielectrophoresis operation is described with reference to FIG. 2 by using as an example the case of detecting *Escherichia coli* contained in a sample solution.

Figure 2:
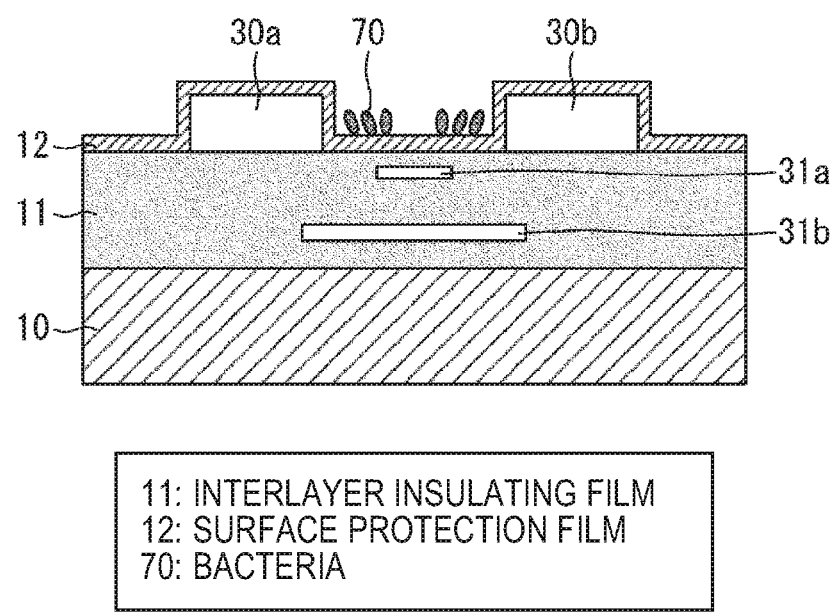
FIG. 2 is an illustration depicting that *Escherichia coli* bacteria are induced to Embodiment 1.

As illustrated in FIG. 2, *Escherichia coli* bacteria are attracted close to an end portion of the dielectrophoresis electrode 31a at which the electric field is stronger and non-uniform. The test target is manipulated to move into an area between the facing electrodes of the measuring electrode pair 30, particularly, into an area close to the electrodes, where the detection sensitivity is relatively high.

Next, effects of the impedance sensor 1 according to Embodiment 1 is described.

Since the impedance sensor 1 is configured by using the LC oscillator 20 positioned at the semiconductor substrate 10, it is possible to achieve impedance measurement at high frequencies of 30 to 200 GHz and the impedance sensor 1 can be suitably used for detecting a biological material. The dielectrophoresis electrode pair 31 is provided as an object different from the measuring electrode pair 30 at the first wiring layer different from the wiring layer at which the measuring electrode pair 30 for impedance is formed. As a result, for example, the problem concerning the related art (refer to PTL 2) described below can be solved. That is, in the related art, the electrode pair 3000 for dielectrophoresis is identical to the electrode pair 3000 for measuring impedance, when impedance is measured while dielectrophoresis is applied, it is necessary to perform application and measurement at the same frequency and amplitude. When a signal at a frequency and an amplitude suitable for impedance measurement is used, dielectrophoresis cannot function during the measurement, and thus, the effect of collecting test targets is weakened. In the case in which an impedance sensor is provided at a semiconductor substrate to integrate a measurement circuit, a signal source, and a function of communicating with other devices at high density, the voltage to which the impedance sensor can respond is only about 0.8 to 3.3 V, although it varies depending on the breakdown voltage of the transistor used in manufacturing processes. On the other hand, the voltage suitable for dielectrophoresis is approximately several volts or more, although it depends on properties of a target biological material and properties of solvent. In this case, a signal at an amplitude suitable for dielectrophoresis cannot be applied to the measuring electrode pair, and as a result, dielectrophoresis cannot be efficiently employed.

In contrast, in the present embodiment, it is possible to manipulate a test target to move to a given position, for example, a position close to the measuring electrode pair 30 at which the detection sensitivity is relatively high.

The measuring electrode pair 30 can be formed in a shape suitable for obtaining a measurement sensitivity and a measurement range suitable for the test target in impedance measurement.

Since the dielectrophoresis electrode pair 31 is formed at a layer (the first wiring layer described above) that is lower than the wiring layer in which the measuring electrode pair 30 for measuring impedance is formed, it is possible to reduce the effect on measurement sensitivity due to the installation of the dielectrophoresis electrode pair 31.

Furthermore, a space with relatively higher detection sensitivity (gain) is secured between the electrodes facing each other and it is possible to manipulate the test target to move into the space. As a result, impedance measurement can be stably performed with high sensitivity. This configuration is effective particularly in the case in which the test target is small relative to the size of the measuring electrode pair 30, for example, in the case in which the test target is a microscopic biological material such as a microorganism or a cell.

Further, in the present embodiment, since the dielectrophoresis electrode pair 31 and the measuring electrode pair 30 individually operate, the dielectrophoresis operation and the measurement operation can be simultaneously performed and it is possible to measure impedance in a frequency range suitable for measurement while the state suitable for dielectrophoresis is maintained.

Moreover, since the impedance sensor 1 is formed at the semiconductor substrate 10, it is possible to integrate at high density peripheral functions such as a function of controlling the sensor, retaining measured values, a processing operation of the measured values, and a function of communicating with other devices.

The dielectrophoresis signal source 50 may be positioned outside the semiconductor substrate 10. In this case, the signal amplitude used in circuit operations for generating and controlling dielectrophoresis signals is not limited by the breakdown voltage of the transistor at the semiconductor substrate 10. By employing the configuration in which the dielectrophoresis signal source 50 is positioned outside the semiconductor substrate 10 as described above, the present embodiment can be applied to the case in which large amplitude is desired for preferable dielectrophoresis operation.

Modified Example of Embodiment 1

Figure 3:
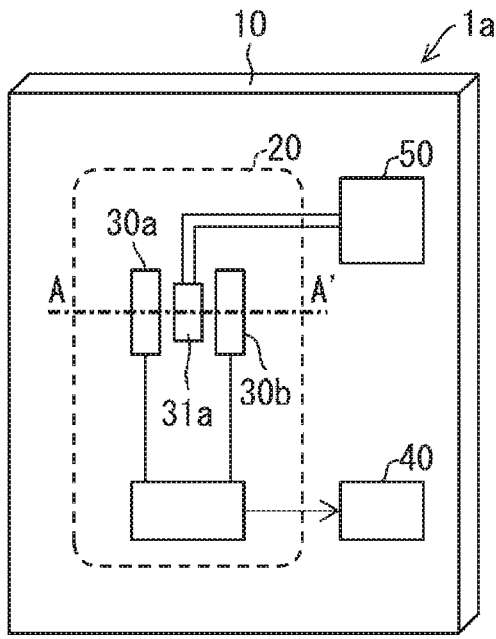
FIG. 3(a) is a block diagram illustrating a configuration of a sensor apparatus according to a modified example of Embodiment 1 of the present invention and FIG. 3(b) is a sectional view taken along line A-A' in FIG. 3(a).
Figure 3:
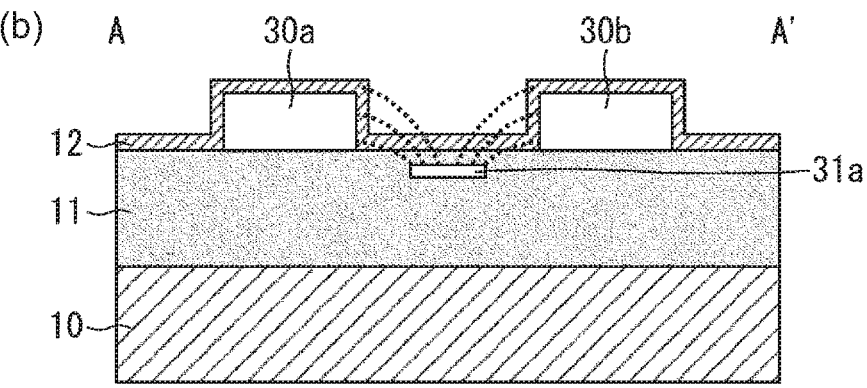

Next, a modified example of Embodiment 1 is described with reference to FIG. 3. FIG. 3(a) is a block diagram illustrating a configuration of a sensor apparatus according to the modified example of Embodiment 1 of the present invention.

An impedance sensor 1a according to the modified example differs from Embodiment 1 in that the dielectrophoresis electrode 31b is omitted. In the present embodiment, it is preferable to use a low resistance substrate, such as silicon, as the semiconductor substrate 10.

Since other configurations according to the modified example are the same as those in Embodiment 1, the other configurations are assigned the same reference characters and detailed description thereof is omitted. Hereinafter, the difference mentioned above is described.

The dielectrophoresis electrode 31a is coupled to the dielectrophoresis signal source 50. A positional relationship between the measuring electrode pair 30 and the dielectrophoresis electrode 31a and wiring layers that are used are described with reference to FIG. 3(b).

As illustrated in FIG. 3(b), the measuring electrode pair 30 is formed at a wiring layer as a bonding pad that is the topmost wiring layer and the thickness of the measuring electrode pair 30 can be greater than the thickness of wires in lower layers. The preferable thickness of the measuring electrode pair 30 is, for example, approximately 4 µm and can be formed of a material such as aluminum.

Additionally, as illustrated in FIG. 3(b), the measuring electrode pair 30 is also covered by a surface protection film 12. It is preferable that the thickness and the material of the surface protection film 12 be the same as those in Embodiment 1. The first wiring layer is covered by the interlayer insulating film 11 and flattened with respect to each wiring layer.

The dielectrophoresis electrode 31a is formed at the first wiring layer between the facing measuring electrodes of the measuring electrode pair 30 (30a and 30b) when the board is viewed from above.

Dotted lines between the dielectrophoresis electrode 31a and the measuring electrode pair 30 in FIG. 3(b) represent lines of electric force in the case of applying a dielectrophoresis signal to the dielectrophoresis electrode 31a.

Next, a dielectrophoresis operation according to the modified example is described. A signal at a suitable frequency and a suitable amplitude is applied by the dielectrophoresis signal source 50 to the dielectrophoresis electrode 31a so as to subject an object under examination to force that moves the object in a direction toward the stronger electric field. The electric field distribution illustrated in FIG. 3(b) appears by applying a dielectrophoresis signal, and the test target is attracted close to an end portion of the dielectrophoresis electrode 31a at which the electric field is stronger and non-uniform. With this configuration, the modified example can obtain the effects similar to those of Embodiment 1.

Embodiment 2

Embodiment 2 of the present invention is described with reference to FIG. 4. FIG. 4(a) is a block diagram illustrating a configuration of an impedance sensor array 2 according to Embodiment 2 of the present invention. The difference between Embodiment 2 and Embodiment 1 is that two impedance sensors (an impedance sensor 1-1 and an impedance sensor 1-2) are disposed at the impedance sensor array 2 and a fluid path 80 is formed over the semiconductor substrate. As the impedance sensors, two impedance sensors that are each identical to the one described in Embodiment 1 are disposed.

Figure 4:
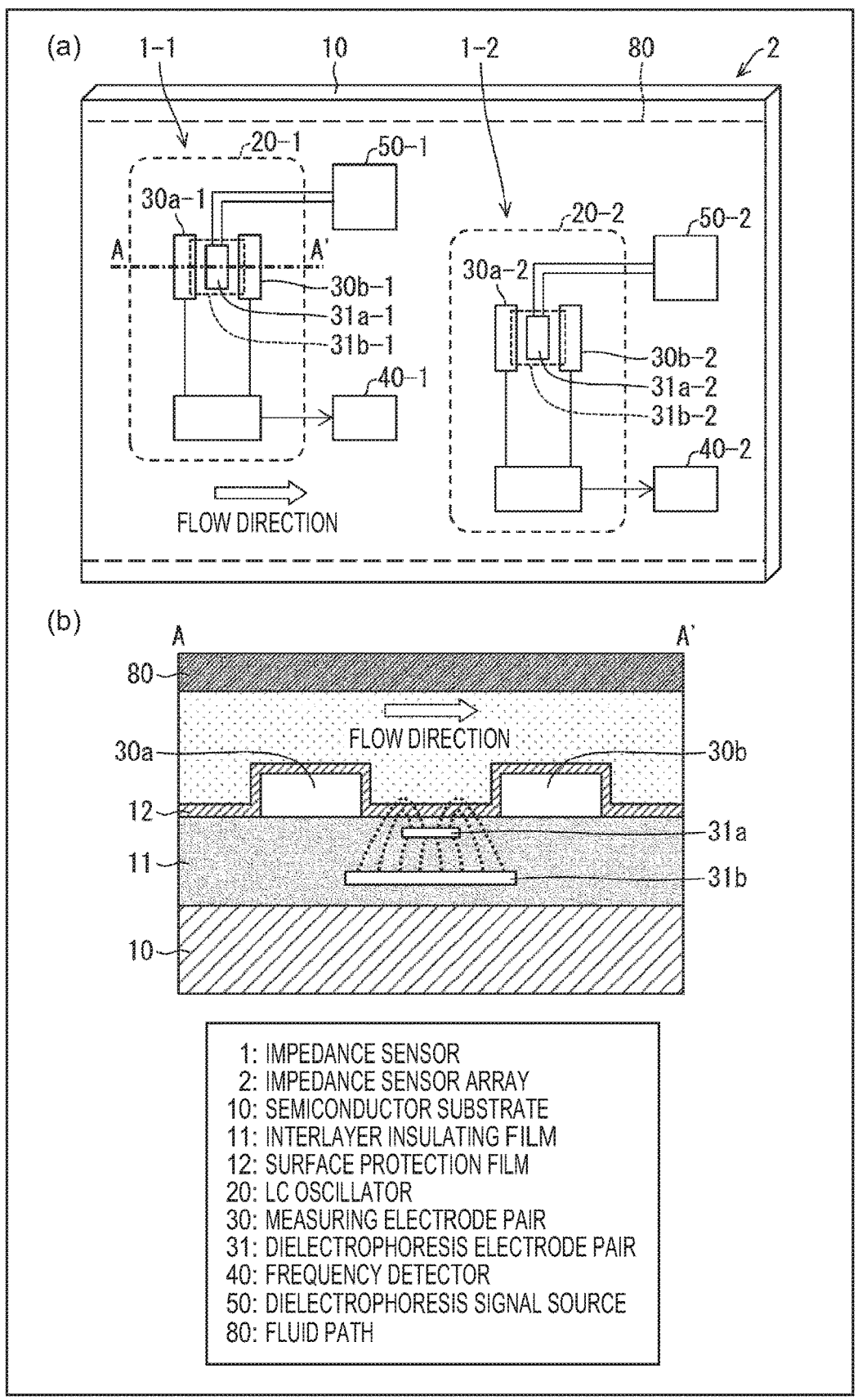
FIG. 4(a) is a block diagram illustrating a configuration of an impedance sensor array according to Embodiment 2 of the present invention and FIG. 4(b) is a sectional view taken along line A-A' in FIG. 4(a).

Concerning the positional relationship among the elements, when viewed from an upstream side of the fluid path 80, the measuring electrode pair 30 and the dielectrophoresis electrode pair 31 of each of the impedance sensors are disposed not to overlap the measuring electrode pair 30 and the dielectrophoresis electrode pair 31 of the other of the impedance sensors; in other words, as illustrated in FIG. 4, the impedance sensor 1-1 and the impedance sensor 1-2 are disposed such that, when viewed from an upstream side of the fluid path, none of the measuring electrode pair 30a-1 and 30b-1, and the dielectrophoresis electrode pair 31a-1 and 31b-1 of the impedance sensor 1-1 overlaps any of the measuring electrode pair 30a-2 and 30b-2 and the dielectrophoresis electrode pair 31a-2, 31b-2 of the impedance sensor 1-2. This is for the purpose of not affecting the downstream sensors by capturing the test target by using the upstream sensors by means of dielectrophoresis with respect to the test target.

While for ease of description the configuration in which two impedance sensors 1 are disposed is used as an example, other configurations in which three or more impedance sensors 1 are disposed may be used. In addition, while the frequency detector 40 and the dielectrophoresis signal source 50 are provided for each impedance sensor 1, the frequency detector 40 and the dielectrophoresis signal source 50 shared by a plurality of impedance sensors 1 may be used.

The fluid path 80 is formed from a material such as glass or polydimethylsiloxane (PDMS).

FIG. 4(b) is a sectional view taken along line A-A' in FIG. 4(a). The height of the fluid path (in other words, the length of the fluid path 80 along a line normal to the semiconductor substrate) can be configured as appropriate to satisfy the following conditions.

The test target smoothly flows in the solvent with which the fluid path is filled Dielectrophoretic force is appropriately applied to the test target The liquid sample flows to pass over the measuring electrode pair 30. In consideration of the efficiency in capturing test targets, it is preferable to set the flow direction at a direction in which the width of the dielectrophoresis electrode 31a is maximized when viewed from an upstream side. It should be noted that it is preferable to set the flow direction as appropriate in consideration of the ease of flow of test targets.

An operation of the impedance sensor array 2 according to Embodiment 2 is described by using as an example the case of measuring the concentration of bacteria contained in liquid. A sample solution containing test target bacteria is caused to pass over the impedance sensor 1 at a fixed flow velocity. When the dielectrophoretic force, the flow velocity, and the height of the fluid path 80 are set in an appropriate relationship, bacteria passing over the dielectrophoresis electrode pair 31 are captured and collected by means of dielectrophoresis. The impedance after a given time elapses, or the changes in impedance during a given time depends on the concentration of microorganisms that exist in the test sample liquid. By performing comparison with the result of impedance measurement by using a reference material containing a known number of microorganisms, the number of microorganisms contained in the test sample liquid can be estimated.

By performing the operation described above, the effects described below can be achieved in Embodiment 2 in addition to the effects achieved in Embodiment 1.

Since new sample material is continuously supplied by using the fluid path 80, it is possible to attract more microorganisms to the measuring electrode pair 30 in comparison to the case of not using the fluid path 80. As a result, the number of microorganisms can be counted with a high sensitivity. Additionally, the height of the fluid path 80 limits the distance between a test target and the measuring electrode pair 30 and the dielectrophoresis electrode pair 31 and the test target is thus efficiently attracted by means of dielectrophoresis; therefore, impedance can be measured by using a little amount of sample liquid.

Furthermore, since a plurality of sensor elements of the same properties are disposed, variations in measurement can be reduced by averaging the measurement results obtained by the respective impedance sensors of the same properties.

When the plurality of sensor elements are different in property from each other due to the effect of manufacturing errors, it is possible to reduce measurement errors by averaging the measurement results obtained by the respective impedance sensors.

Embodiment 2 may be applied to specification of properties of a single cell. Single cells are individually affixed to the disposed impedance sensors 1 and impedance measurement are performed for the plurality of cells. In this case, it is possible to identify a cell having a particular property among many cells. Additionally, since many cells are collectively measured, statistical information such as mean and variance can be obtained with regard to properties of cells.

Embodiment 3

Figure 5:
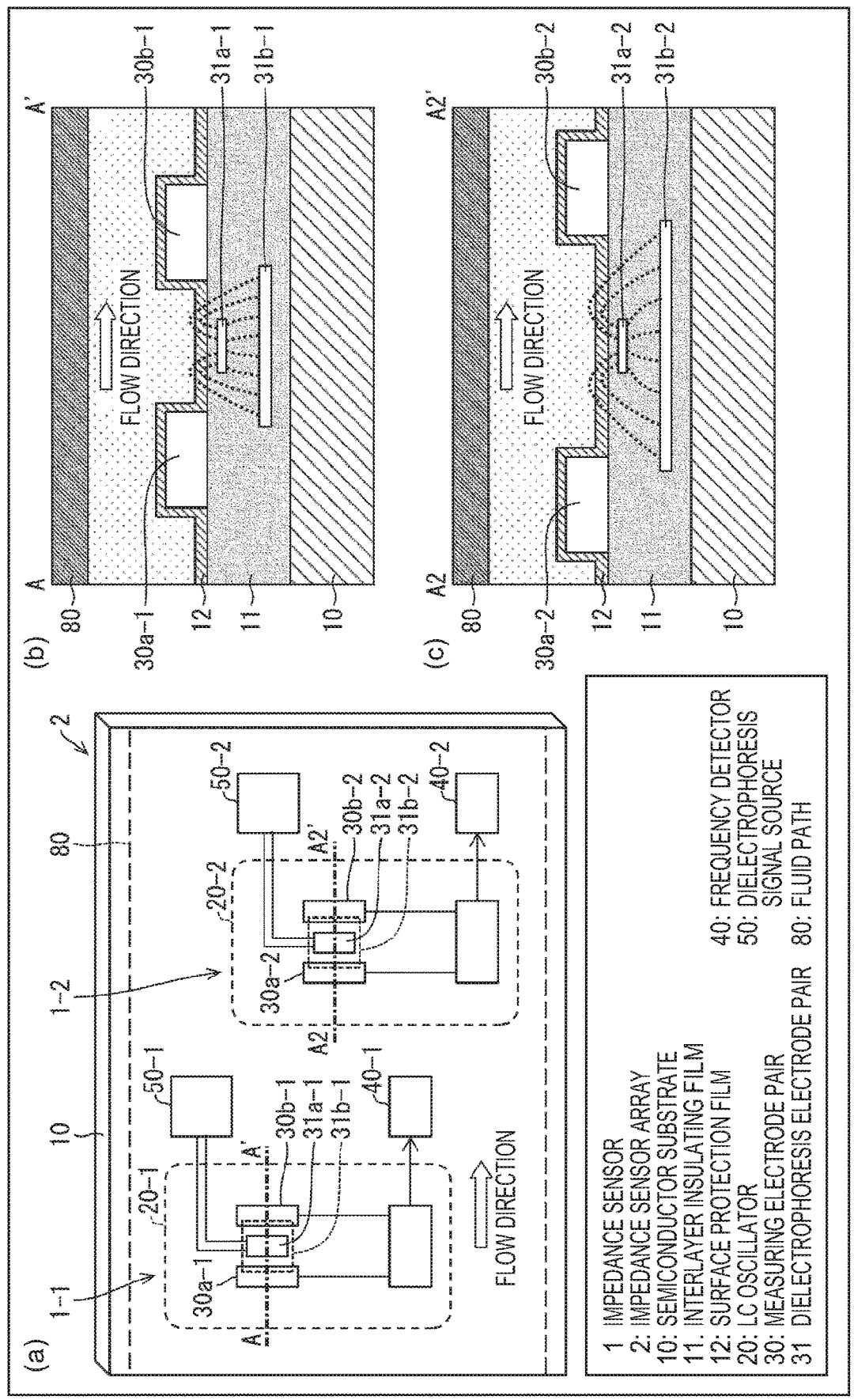
FIG. 5(a) is a block diagram illustrating a configuration of an impedance sensor array according to Embodiment 3 of the present invention.
FIG. 5(b) is a sectional view taken along line A-A' in FIG. 5(a)
FIG. 5(c) is a sectional view taken along line A2-A2' in FIG. 5(a).

As a modified example of Embodiment 2, in the disposed impedance sensors 1, the measuring electrode pair 30 and the dielectrophoresis electrode pair 31 in different shapes may be provided. FIG. 5 is a block diagram illustrating a configuration of an impedance sensor array 2 according to Embodiment 3 of the present invention. The difference to Embodiment 2 is that there are variations in the spacing between two measuring electrodes of the measuring electrode pair 30. In the example illustrated in FIG. 5, the spacing of the measuring electrode pair 30 on the right side is wider than the spacing of the measuring electrode pair 30 on the left side.

As described above, since the spacing between two measuring electrodes of the measuring electrode pair 30 varies, the two impedance sensors are different in property from each other.

When the impedance sensor array 2 is used for measuring the concentration of bacteria, the number of bacteria that can be captured between the measuring electrode pair 30 and detected is larger for the right one than for the left one. As described above, by disposing a plurality of impedance sensors 1 different in property from each other (more specifically, a plurality of impedance sensors 1 different in the range of the countable number of bacteria from each other), in comparison to the case of disposing the impedance sensors 1 of one type, it is possible to expand the dynamic range regarding the measurable concentration of bacteria. While the description above has been made with the use of the impedance sensor array 2 composed of two impedance sensors 1 different in the spacing of the measuring electrode pair 30 from each other, the impedance sensor array 2 may be constituted by three or more impedance sensors 1.

Embodiment 4

Figure 6:
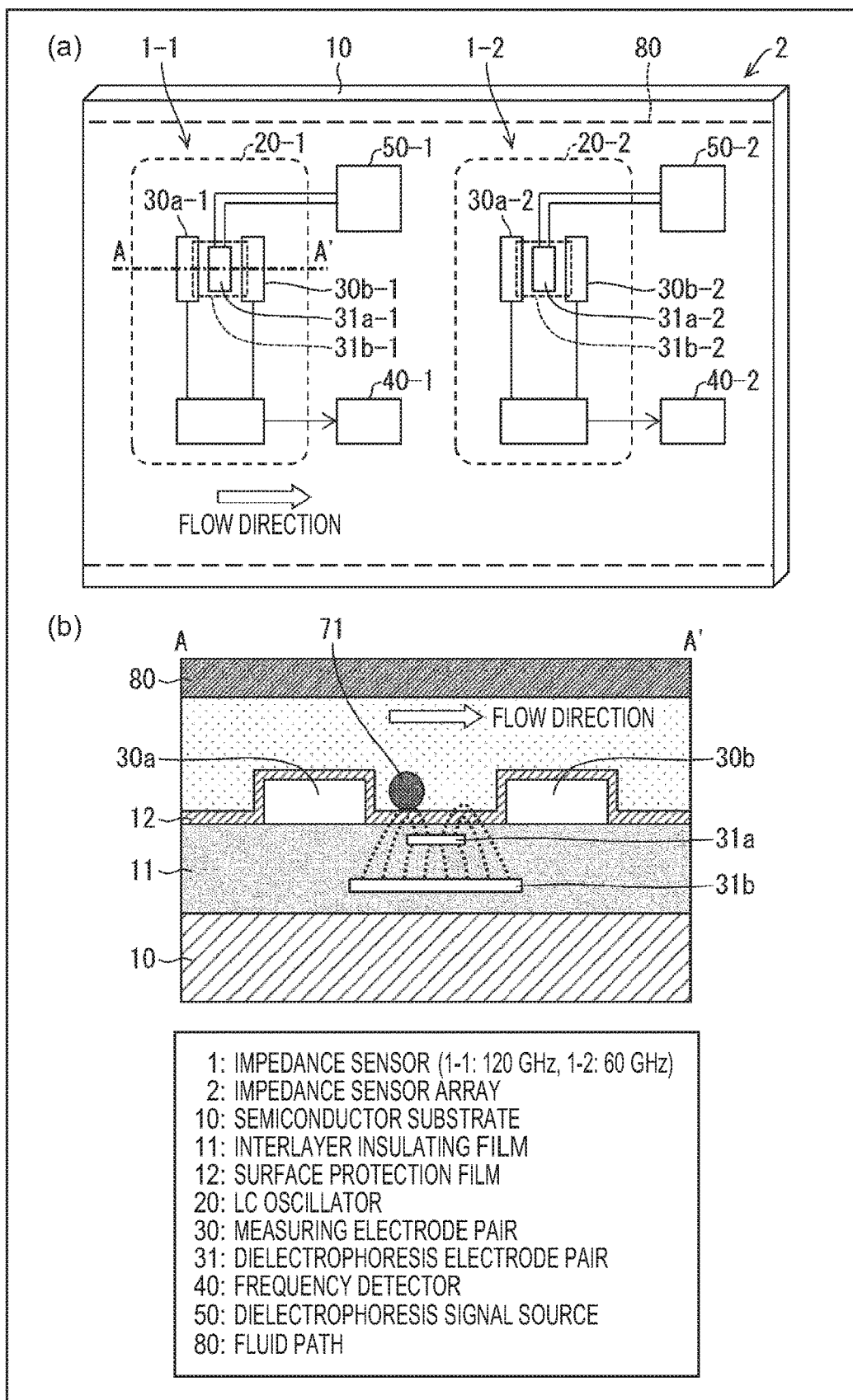
FIG. 6(a) is a block diagram illustrating a configuration of an impedance sensor array according to Embodiment 4 of the present invention and FIG. 6(b) is a sectional view taken along line A-A' in FIG. 6(a).

As another modified example of Embodiment 2, the disposed impedance sensors 1 may include one that uses a different frequency for measuring impedance. FIG. 6 is a block diagram illustrating a configuration of an impedance sensor array 2 according to Embodiment 4 of the present invention. The difference to Embodiment 2 is that, with regard to the value of frequency for measuring impedance (measurement frequency), the impedance sensor 1-1 and the impedance sensor 1-2 use different frequencies, 120 GHz and 60 GHz, respectively. The impedance sensor 1-2 is positioned such that the impedance sensor 1-2 is situated downstream with respect to the impedance sensor 1-1 and test targets released from the dielectrophoresis electrode 31a-1 pass over the dielectrophoresis electrode 31a-2.

Figure 7:
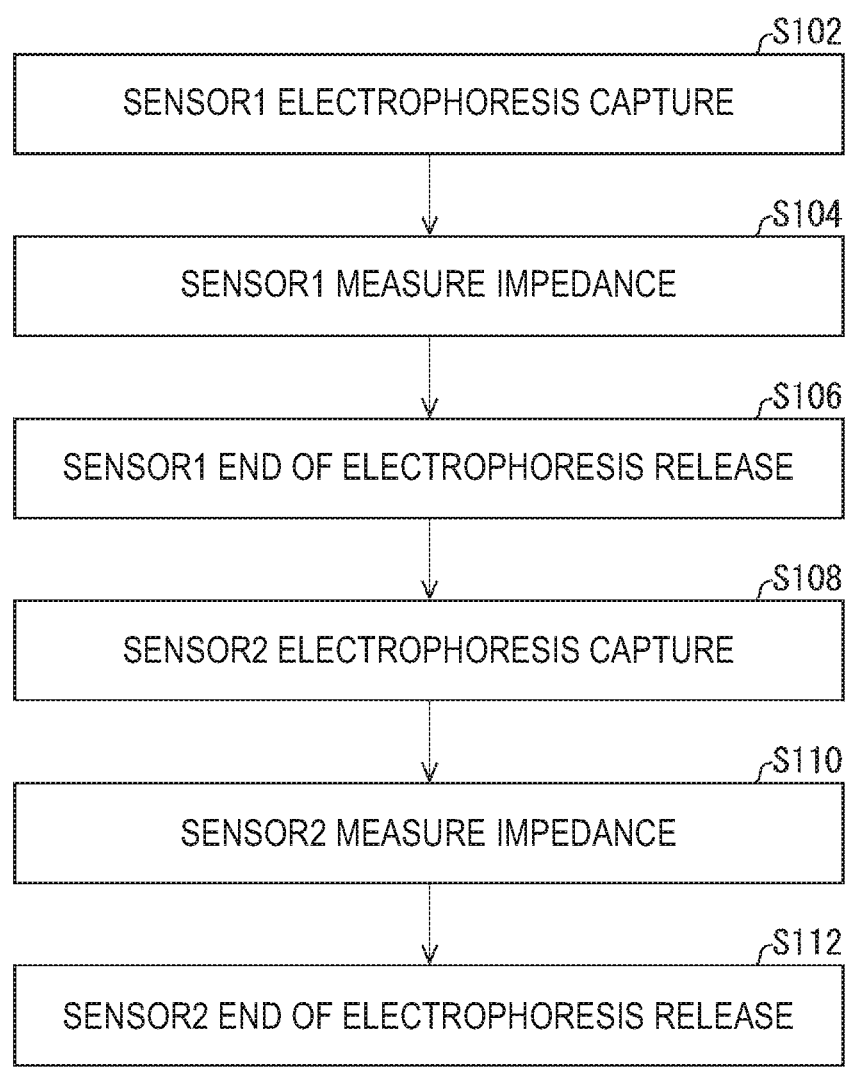
FIG. 7 illustrates an operating procedure of the impedance sensor array according to Embodiment 4 of the present invention.

An operating procedure of the impedance sensor array 2 according to Embodiment 4 of the present invention is described with reference to FIG. 7. In the following procedure, the control of the impedance sensor array 2 may be performed via manual operation carried out by a measuring person or performed by a control apparatus not illustrated in the drawing without manual operation carried out by a measuring person.

(Step S102)

First, in step S102, to the impedance sensor 1-1, a signal is supplied from the dielectrophoresis signal source 50-1, and as a result, a test target is captured close to the dielectrophoresis electrode 31a-1.

(Step S104)

Subsequently, for the test target captured in step S102, impedance measurement at 120 GHz is performed in step S104.

(Step S106)

After the measurement in step S104, in step S106, by controlling the dielectrophoresis signal source 50-1, the signal is stopped or a signal at a frequency that induces negative dielectrophoretic force is supplied. With this operation, the test target is released from the dielectrophoresis electrode 31*a*-1. The released test target is caused to flow downstream along the fluid path 80.

(Step S108)

Next, in step S108, to the impedance sensor 1-2, a signal is supplied from the dielectrophoresis signal source 50-2, and as a result, the test target is captured close to the dielectrophoresis electrode 31*a*-2.

(Step S110)

Subsequently, for the test target captured in step S108, impedance measurement at 60 GHz is performed in step S110.

(Step S112)

Next, in step S112, by controlling the dielectrophoresis signal source 50-2, the signal is stopped or a signal at a frequency that induces negative dielectrophoretic force is supplied. With this operation, the test target is released from the dielectrophoresis electrode 31*a*-2. The released test target is caused to flow downstream along the fluid path 80.

With the operations above, an impedance at 120 GHz and an impedance at 60 GHz are measured for the test target. As a result, in addition to the effects achieved in the first and second embodiments, the state of test target can be evaluated from different perspectives. While the case of measuring impedance by using two impedance sensors 1 and two levels of frequency is described, with the aim of performing evaluation from more different perspectives, three or more impedance sensors 1 may be disposed and measuring impedance may be performed at three or more levels of frequency.

Embodiment 5

Figure 8:
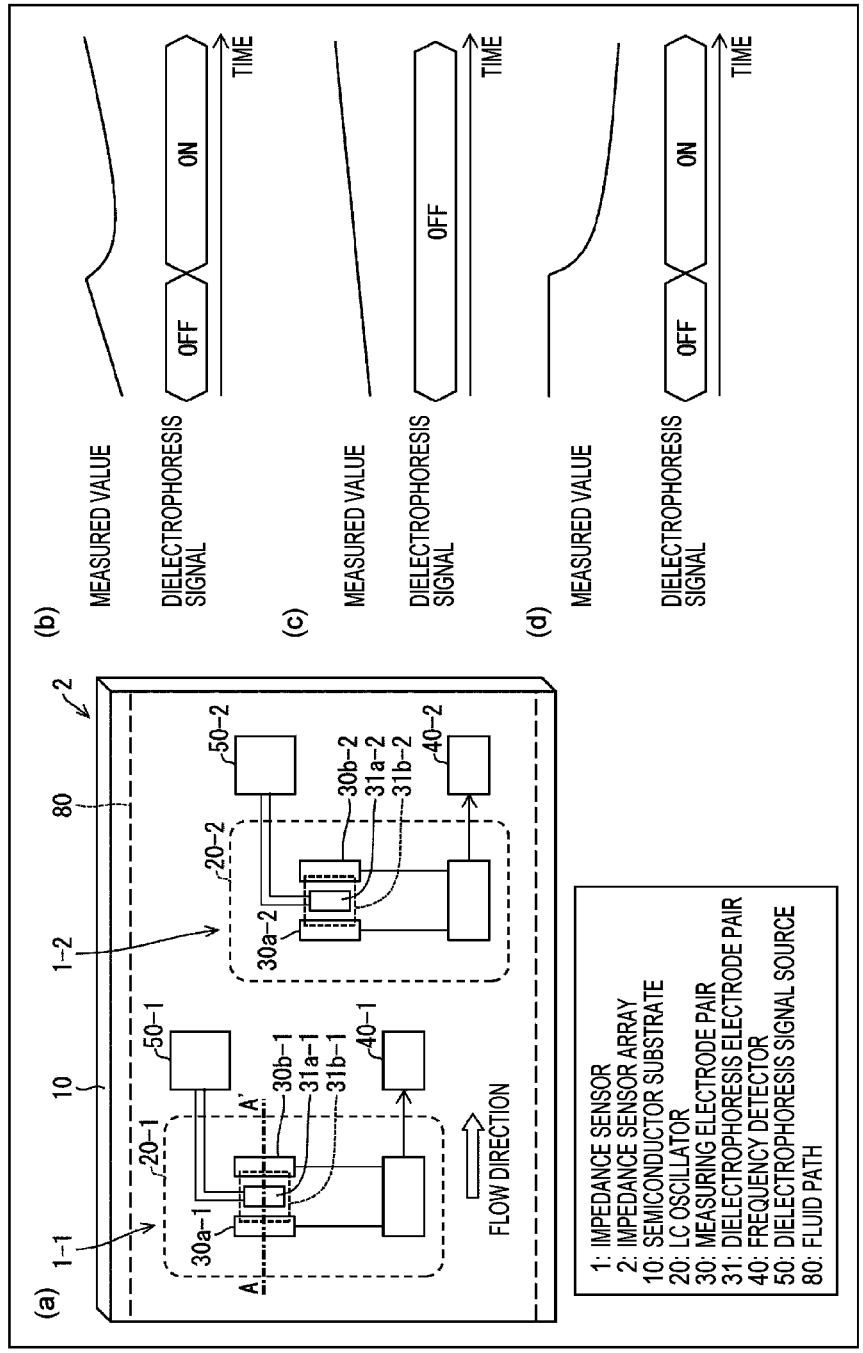
FIG. 8(a) is a block diagram illustrating a configuration of an impedance sensor array according to Embodiment 5 of the present invention.
FIGS. 8(b) and 8(c) are conceptual diagrams regarding a measurement procedure of dielectrophoresis measurement.
FIG. 8(d) is a conceptual diagram regarding adjusted measurement values of an impedance sensor.
Figure 9:
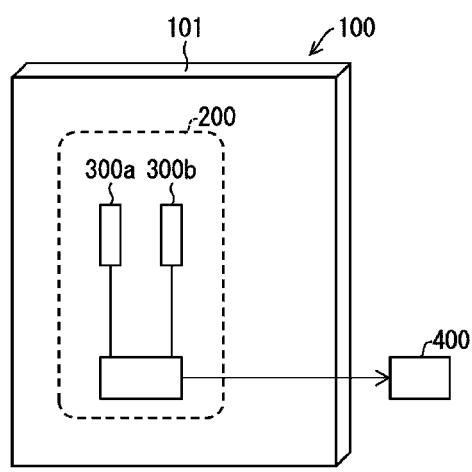
FIG. 9 is an explanatory diagram illustrating a configuration of an impedance sensor according to a first related-art example.
Figure 10:
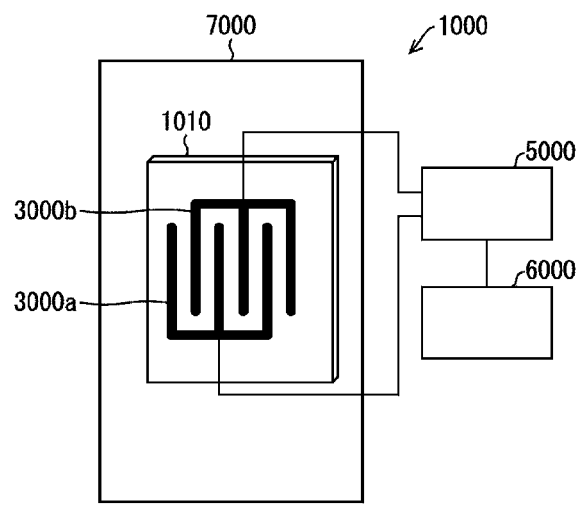
FIG. 10 is an explanatory diagram illustrating a configuration of an impedance sensor according to a second related-art example.

As still another modified example of Embodiment 2, in the disposed impedance sensors 1, the one that does not apply dielectrophoresis signals may be provided. FIG. 8(*a*) is a block diagram illustrating a configuration of the impedance sensor array 2 according to Embodiment 5 of the present invention. FIGS. 8(*b*) and 8(*c*) are conceptual diagrams regarding a measurement procedure of dielectrophoresis measurement. FIG. 8(*d*) is a conceptual diagram regarding adjusted measurement values of an impedance sensor. As illustrated in FIG. 8(*a*), an impedance sensor array 2 according to Embodiment 5 is identical to that of Embodiment 2.

Hereinafter, the case is considered where temperature of solvent with which the sample is supplied fluctuates due to the effects of, for example, a measurement environment. FIG. 8(*b*) illustrates that the measurement value varies while a dielectrophoresis signal is applied to the impedance sensor 1-1 and the test target is collected. In contrast, since no dielectrophoresis signal is applied to the impedance sensor 1-2, the measurement results of impedance 1-2 does not vary due to the presence of the test target. The impedance sensor 1-2 to which no dielectrophoresis signal is applied can be used for detecting fluctuations in impedance of solvent caused together with fluctuations in temperature. By using the measurement values obtained by the impedance sensor 1-2, as illustrated in FIG. 8(*d*), values can be obtained by changing the measurement values of the impedance sensor 1-1 by the degrees cause by the fluctuations in temperature of solvent.

As described above, when at the time of measurement impedance of solvent fluctuates due to, for example, fluctuations in temperature of solvent, the effect can be adjusted, and as a result, the effect of environmental fluctuations can be mitigated. While fluctuations in temperature of solvent is used as an example in the description, it is effective against other factors such as fluctuations in power source voltage and vibrations.

While in the description above the case of counting the number of microorganisms is used as an example, the example should not be construed in a limiting sense and the present invention may be applied to the case of specifying properties of another biological material such as a cell.

The present invention is not limited to the embodiments described above and various changes can be made within the scope described in the claims. Embodiments constituted by any combination of technical means disclosed in the different embodiments are embodied in the scope of the present invention. Furthermore, by combining technical means disclosed in the embodiments with each other, a novel technical feature may be formed.

While the size, the frequency, the amplitude, and the like have been described by using specific numbers, they are not particularly limited to those numerical values. Moreover, while a sensor that measures the permittivity of test target in accordance with the oscillation frequency of the LC oscillator 20 is used as an example of the impedance sensor, as might be expected, other modes such as a sensor that measures impedance in accordance with the amplitude and the phase of current and voltage applied to the measuring electrode pair 30 are also suitably utilized.

CONCLUSION

A sensor according to a first aspect of the present invention includes a measuring electrode pair formed at a wiring layer in a multilayer-wiring circuit board and one or more dielectrophoresis electrodes formed at another wiring layer lower than the wiring layer.

With this configuration, it is possible to measure impedance of a target material stably with high sensitivity.

In the sensor according to a second aspect of the present invention, with respect to the first aspect, the multilayer-wiring circuit board may be a semiconductor substrate.

With this configuration, the circuit operation at high frequencies is achievable, and thus, the measuring electrode pair can be suitably used for impedance measurement at high frequencies.

In the sensor according to a third aspect of the present invention, with respect to the first or second aspect, the measuring electrode pair may be covered by a surface protection film and the thickness of the measuring electrode pair may be greater than the thickness of the surface protection film.

With this configuration, a space for positioning a test target is secured in an area with relatively high detection sensitivity (gain) between electrodes.

In the sensor according to a fourth aspect of the present invention, with respect to any one of the first to third aspects, a fluid path may be formed over the multilayer-wiring circuit board.

With this configuration, in comparison to the case of not using the fluid path, it is possible to attract more target materials between the measuring electrodes. As a result, the number of target materials can be counted with a higher sensitivity.

A sensor array according to a fifth aspect of the present invention includes a plurality of sensors in a single multilayer-wiring circuit board, with respect to any one of the first to third aspects, in which each of the plurality of sensors may be the sensor according to any one of the first to third aspects.

With this configuration, variations in measurement can be reduced by averaging the measurement results obtained by the respective impedance sensors.

In the sensor array according to a sixth aspect of the present invention, with respect to the fifth aspect, at least one of the plurality of sensors may be different in property from another of the plurality of sensors.

With this configuration, in comparison to the case of disposing sensors of one type, it is possible to expand the dynamic range regarding the measurable concentration of target material.

In the sensor array according to a seventh aspect of the present invention, at least one of the plurality of sensors may be different in measurement frequency from another of the plurality of sensors.

With this configuration, the state of target material as a test target can be evaluated from different perspectives.

In the sensor array according to an eighth aspect of the present invention, a fluid path is formed over the single multilayer-wiring circuit board, and when viewed from an upstream side of the fluid path, the measuring electrode pair and the dielectrophoresis electrode of each of the plurality of sensors are disposed not to overlap the measuring electrode pair and the dielectrophoresis electrode of another of the plurality of sensors.

With this configuration, it is possible to not affect the downstream sensors by capturing the target material by using the upstream sensors by means of dielectrophoresis with respect to the target material.

REFERENCE SIGNS LIST 1, 1a impedance sensor
2 impedance sensor array
10 semiconductor substrate
11 interlayer insulating film
12 surface protection film
20 LC oscillator
30 (30a, 30b) measuring electrode pair
31 (31a, 31b) dielectrophoresis electrode pair
40 frequency detector
50 dielectrophoresis signal source
70 bacteria
80 fluid path
100, 1000 impedance sensor (related-art example)
101 semiconductor substrate (related-art example)
1010 glass substrate (related-art example)
200, 2000 LC oscillator (related-art example)
300, 3000 measuring electrode pair (related-art example)
400 frequency detection circuit (related-art example)
5000 dielectrophoresis signal source (related-art example)
6000 measuring unit (related-art example)
7000 cell (related-art example)

The invention claimed is:

1. A sensor array comprising a plurality of sensors in a single multilayer-wiring circuit board, wherein
each of the plurality of sensors comprises:
a measuring electrode pair formed at a wiring layer in the single multilayer-wiring circuit board; and
one or more dielectrophoresis electrodes formed at another wiring layer lower than the wiring layer, wherein the measuring electrode pair is covered by an insulating film and a thickness of the measuring electrode pair is greater than a thickness of the insulating film,
a fluid path is formed over the single multilayer-wiring circuit board, and
when viewed from an upstream side of the fluid path, the measuring electrode pair and the one or more dielectrophoresis electrodes of each of the plurality of sensors are disposed not to overlap the measuring electrode pair and the dielectrophoresis electrode of another of the plurality of sensors.

2. The sensor array according to claim 1, wherein at least one of the plurality of sensors is different in property from another of the plurality of sensors.

3. The sensor array according to claim 1, wherein at least one of the plurality of sensors is different in measurement frequency from another of the plurality of sensors.

* * * * *